United States Patent
Bhaskaran et al.

(10) Patent No.: US 9,956,301 B2
(45) Date of Patent: May 1, 2018

(54) COMPLEX OF GARCINOL, CYCLODEXTRIN AND METHOD THEREOF

(71) Applicant: Indus Biotech Private Limited, Maharashtra (IN)

(72) Inventors: Sunil Bhaskaran, Maharashtra (IN); Mohan Vishwaraman, Maharashtra (IN)

(73) Assignee: Indus Biotech Private Limited, Maharashtra (IN)

( * ) Notice: Subject to any disclaimer, the term of this patent is extended or adjusted under 35 U.S.C. 154(b) by 0 days. days.

(21) Appl. No.: 14/593,882

(22) Filed: Jan. 9, 2015

(65) Prior Publication Data

US 2015/0196669 A1    Jul. 16, 2015

Related U.S. Application Data

(62) Division of application No. 13/016,541, filed on Jan. 28, 2011.

(30) Foreign Application Priority Data

Dec. 9, 2010  (IN) .......................... 3765/CHE/2010

(51) Int. Cl.
| | |
|---|---|
| A61K 31/122 | (2006.01) |
| A61K 47/48 | (2006.01) |
| C07C 45/79 | (2006.01) |
| B82Y 5/00 | (2011.01) |
| C07C 49/835 | (2006.01) |
| C08B 37/16 | (2006.01) |
| A61K 47/69 | (2017.01) |

(52) U.S. Cl.
CPC ...... *A61K 47/48969* (2013.01); *A61K 31/122* (2013.01); *A61K 47/6951* (2017.08); *B82Y 5/00* (2013.01); *C07C 45/79* (2013.01); *C07C 49/835* (2013.01); *C08B 37/0015* (2013.01); *C07B 2200/01* (2013.01); *C07C 2602/46* (2017.05)

(58) Field of Classification Search
None
See application file for complete search history.

(56) References Cited

U.S. PATENT DOCUMENTS

| | | | | |
|---|---|---|---|---|
| 6,464,988 | B1 * | 10/2002 | Gidwani | A61K 47/48969 424/400 |
| 6,960,300 | B2 | 11/2005 | Majeed et al. | |
| 2005/0051483 | A1 * | 3/2005 | Majeed | A23L 33/105 210/634 |
| 2006/0253100 | A1 | 11/2006 | Burright et al. | |
| 2007/0254961 | A1 | 11/2007 | Tapas Kumar et al. | |
| 2008/0152709 | A1 | 6/2008 | Bortz | |

FOREIGN PATENT DOCUMENTS

JP    2003231607 A  *  8/2003

OTHER PUBLICATIONS

Tilak-Jain, J. A.; et al. "Cardioprotective and other beneficial effects of some Indian medicinal plants" J. Clin. Biochem. Nutr., 2006, v. 38, p. 9-18.*
Darji, K. K.; et al. "Evaluation of Antioxidant and antihyperlipidemic activity of extract of garcinia indica" International Journal of Pharmaceutical Sciences and Research, 2010, v. 1 (12), 175-181.*
Spector, A. A. "HIV protease inhibitors and Hyperlipidemia: A fatty acid connection" Arteriosclerosis, Thrombosis, and Vascular biology, 2006, v. 26, pp. 7-9.*
Vasdev, S.; et al. "Modulation of oxidative stress-induced changes in hypertension and atherosclerosis by antioxidants" Exp. Clin. Cardiol., 2006, v. 11, iss. 3, pp. 206-216.*
Garcinol MSDS sheet, Enzo life sciences, 2009, http://www.funakoshi.co.jp/data/datasheet/MOL/GR343.pdf.*
Tiwari, G.; et al. "Cyclodextrins in delivery systems: Applications" Journal of Pharmacy & Bioallied Sciences, 2010, 72-79.*
Padhye, S.; et al. "Emerging role of Garcinol, the antioxidant chalcone from Garcinia indica Choisy and its synthetic analogs" Journal of Hematology & Oncology, 2009, no pagination.*
Loftsson, et. al. "Cyclodextrins in Drug Delivery" Expert Opinion on Drug Delivery, 2005, p. 335-351.*
Uekama, et al. "Cyclodextrin in Drug Carrier Systems" Chem. Rev. 1998, 98, 2045-2076.*
Arai, M. et al., "Mechanism of Doxorubicin-Induced Inhibition of Sarcoplasmic Reticulum Ca2•-ATPase Gene Transcription," *Circulation Research*, Jan. 2000, pp. 8-14.
Badr-Eldin, S. M.; et al. "Inclusion complexes of tadalafil with natural and chemically modified B-cyclodextrins. 1: Preparation and in vitro evaluation." European Journal of Pharmaceutics and Biopharmaceutics, 2008, v. 70, Abstract.
Bristow, M. R. et al., "Pharmacology and Inotropic Potential of Forskolin in the Human Heart," Journal of Clinical Investigation, 1984, v. 74, 212-223.
Krishnamurthy, N. et al., "On the Structures of Garcinol, Isogarcinol and Camboginol," *Tetrahedron Letters*, 1981, pp. 793-796, vol. 22.
Loftsson, T. et al. Cyclodextrins in drug delivery. Expert Opinion in Drug Delivery 2005, v. 2, issue 2, pp. 335-351.

(Continued)

*Primary Examiner* — Mina Haghighatian
*Assistant Examiner* — Erin Hirt
(74) *Attorney, Agent, or Firm* — Fenwick & West LLP

(57) ABSTRACT

The present disclosure discloses a pharmaceutical molecule of Garcinol chemically complexed with cyclodextrins and the use of the complexed molecule in prevention and management of cardiac dysfunction induced by chemotherapy, drugs and/or other insults to the heart caused by lifestyle and disease conditions. The disclosure also relates to a method of extraction and purification of high yield of 95-99% pure Garcinol from *Garcinia* species and a method of chemically complexing Garcinol with cyclodextrins to improve its stability and bioavailability.

11 Claims, 1 Drawing Sheet

(56) References Cited

OTHER PUBLICATIONS

Takizawa, T. et al., "Transcription of the SERCA2 Gene is Decreased in Pressure-overloaded Hearts: A Study Using In Vivo Direct Gene Transfer into Living Myocardium," *Journal of Molecular and Cellular Cardiology*, 1999, pp. 2167-2174, vol. 31.
United States Office Action, U.S. Appl. No. 13/016,541, dated Jul. 1, 2014, 12 pages.
United States Office Action, U.S. Appl. No. 13/016,541, dated Dec. 23, 2013, 13 pages.
United States Office Action, U.S. Appl. No. 13/016,541, dated May 9, 2013, 13 pages.
United States Office Action, U.S. Appl. No. 13/016,541, dated Oct. 25, 2012, 13 pages.

\* cited by examiner

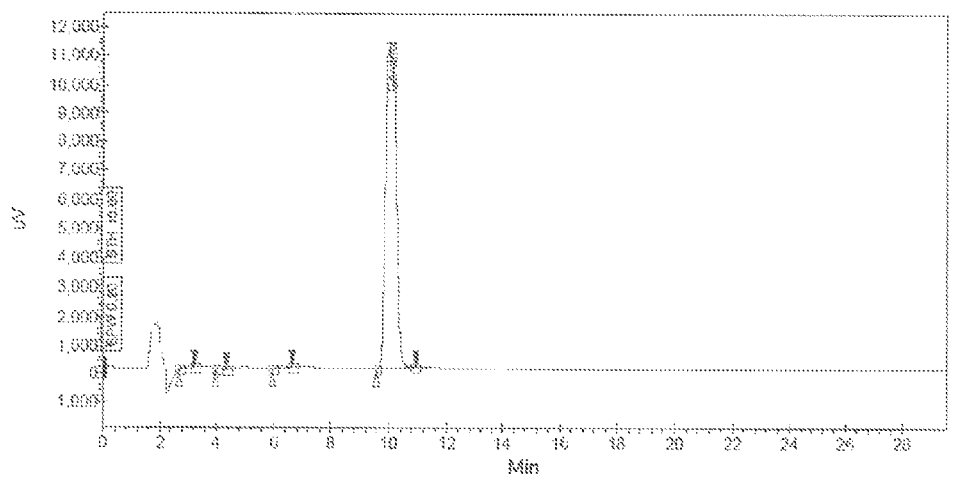

COMPLEX OF GARCINOL, CYCLODEXTRIN AND METHOD THEREOF

RELATED APPLICATIONS

This application is a divisional of U.S. patent application Ser. No. 13/016,541, filed Jan. 28, 2011 which claims priority to Indian Patent Application No. 3765/CHE/2010, filed Dec. 9, 2010, both of which are incorporated by reference herein in their entirety.

TECHNICAL FIELD

The present disclosure discloses a pharmaceutical molecule of Garcinol chemically complexed with cyclodextrins and the use of the complexed molecule in prevention and management of cardiac dysfunction induced by chemotherapy, drugs and/or other insults to the heart caused by lifestyle and disease conditions. The disclosure also relates to a method of extraction and purification of high yield of 95-99% pure Garcinol from *Garcinia* species and a method of chemically complexing Garcinol with cyclodextrins to improve its stability and bioavailability.

BACKGROUND

Doxorubicin is a cytotoxic anthracycline antibiotic used as a first-line chemotherapeutic agent in treatment of various neoplastic conditions like lymphoblastic leukemia, myoblastic leukemia, breast and ovarian carcinoma etc. Despite the wide use of Doxorubicin, cardiotoxicity side effect remains a major concern. The mechanism of Doxorubicin induced cardiotoxicity is associated with impaired $Ca^{2+}$ handling in the sarcoplasmic reticulum (SR) reducing the cardiac function. Sarcoplasmic reticulum $Ca^{2+}$-ATPase 2 (SERCA2) is a major $Ca^{2+}$ transport protein in the SR.

Arai et. al. (2000), has demonstrated that expression of mRNA encoding SERCA2 and the ability of the SERCA2 protein to take up $Ca^{2+}$ were markedly decreased in Doxorubicin treated heart. This reduction in intracellular $Ca^{2+}$ leads to reduction in heart rate due to reduced excitability of pacemaker cells in the sinoatrial node and other cells in the cardiac conduction system. Doxorubicin treatment induces a progressive and severe deterioration of the repolariztion phase in the ECG. This is indicated by an increased ST interval. A prolonged QT interval indicates ventricular tachyarrhythmias and a risk factor for sudden death. Administration of Doxorubicin also increases oxidative stress in the heart. Histopathological changes in doxorubicin treatment causes extensive vacuolization in the cytoplasm of myocardial cells, doxorubicin induced cardiac damage and marked edema, disorganized myocardial fibers, and necrosis.

Cardiotoxicity is a major side effect not limited to Doxorubicin. Isoproterenol is a non-selective beta-agonist used in treating heart block or bradycardia. The positive inotropic effect of isoproterenol is useful in increasing the strength of muscular contraction however it has associated cardiotoxic side effects namely tachycardia or elevated heart rate, cardiac dysrhythmias, increased risk of myocardial infarction and death due to cardiac arrest.

Digitalis another positive inotropic agent used in treatment of atrial fibrillation, flutter and congestive heart failure also has dose dependent toxicity. At high doses, digitalis induces irregular heartbeat, ectopic atrial tachycardia and cardiac arrest. The side effects of this drug greatly outweigh its therapeutic efficacy.

Cardiac dysfunction induced by drug substances result in conditions namely arrhythmias, atrial fibrillation, tachycardia or bradycardia etc which subsequently results in heart failure. Prevention of cardiac dysfunction by protecting the heart from toxic side effects of will greatly enhance the efficacy of these drug substances.

Apart from drug induced cardiac dysfunction, insults to the heart caused by lifestyle and disease conditions like stenosis, hypertension, atherosclerosis, myocardial infarction, ischemic heart disease, cardiomyopathy etc., also result in reduced cardiac function. This is due to an increased peripheral resistance which in turn increases the pressure load on the heart. Takizawa et. al. (1999), has reported that under these conditions of pressure-overload there is a reduction in transcription of SERCA2 mRNA expression which decreases SERCA2 protein concentration and decreases $Ca^{2+}$ uptake in the SR.

Garcinol is a polyisoprenylated benzophenone derivative present in the fruit rinds of *Garcinia* species namely *Garcinia indica* (common name 'Kokum') and *Garcinia cambogia* (common name 'Gombogee') at 2-3% by weight. Literature reports extraction of Garcinol from *Garcinia indica* using aqueous organic solvents (Krishnamurthy et al., 1981) with a yield ranging from 0.8-1.5% and assay purity of only 50-70%. Garcinol is a yellow solid substance with a molecular weight of 602.8 and molecular formula $C_{38}H_{50}O_6$.

STATEMENT OF DISCLOSURE

Accordingly the present disclosure relates to a complex of Garcinol and Cyclodextrin; a method for preparation of a complex of Garcinol and Cyclodextrin, said method comprising acts of, dissolving the Garcinol in a solvent with the Cyclodextrin to obtain a mixture, refluxing the mixture to form a clear solution, cooling the clear solution to obtain crystals of the complex of the Garcinol and the Cyclodextrin and filtering and drying the crystals to obtain the complex of Garcinol and Cyclodextrin; Garcinol of purity ranging from about 95% to about 99%; a method for extracting Garcinol, said method comprising acts of, shredding dried rind of *Garcinia Indica* or *Garcinia Cambogia* or combination thereof, extracting the shredded rind using suitable solvent, filtering to remove the cellulosic material and obtain clear solution, passing the clear solution through absorbent column to segregate into different fractions and obtain yellow coloured fraction, concentrating the yellow coloured fraction to obtain a waxy material, treating the waxy material with a suitable solvent; filtering and drying the treated waxy material to obtain the Garcinol; a composition comprising complex of Garcinol and Cyclodextrin along with pharmaceutically acceptable excipients; a method of improving condition of cardiac dysfunction, said method comprising act of providing pharmaceutically acceptable amount of complex to a subject in need thereof, wherein the subject is an animal, including human being; a composition comprising pharmaceutically acceptable amount of complex of Garcinol and Cyclodextrin and any other compound which can improve condition of cardiac dysfunction or any composition comprising thereof and a method of managing and treating conditions of cardiac dysfunction said method comprising act of administering pharmaceutically effective amount of complex of the present invention or a composition of the present invention to a subject in need thereof.

BRIEF DESCRIPTION OF THE ACCOMPANYING FIGURE

In order that the disclosure may be readily understood and put into practical effect, reference will now be made to exemplary embodiments as illustrated with reference to the accompanying FIGURE. The FIGURE together with a detailed description below, are incorporated in and form part of the specification, and serve to further illustrate the embodiments where:

FIG. 1: shows HPLC of Garcinol.

DETAILED DESCRIPTION OF THE DISCLOSURE

The present disclosure is in relation to a complex of Garcinol and Cyclodextrin.

In an embodiment of the present invention, the mole ratio of the Garcinol to the Cyclodextrin ranges from about 1:1 to about 1:4.5.

In another embodiment of the present invention, the complex is a chemical complex.

In still another embodiment of the present invention, the Garcinol is of purity ranging from about 95% to about 99%.

In still another embodiment of the present invention, the Cyclodextrin is selected from a group comprising α-cyclodextrin, β-cyclodextrin, 2-Hydroxy-propyl-β-cyclodextrin and derivatives thereof.

In still another embodiment of the present invention the Cyclodextrin is β-cyclodextrin.

In still another embodiment of the present invention the Cyclodextrin is suitable derivative of β-Cyclodextrin.

The present invention is also in relation to a method for preparation of a complex of Garcinol and Cyclodextrin, said method comprising acts of,
 a) dissolving the Garcinol in a solvent with the Cyclodextrin to obtain a mixture;
 b) refluxing the mixture to form a clear solution;
 c) cooling the clear solution to obtain crystals of the complex of the Garcinol and the Cyclodextrin; and
 d) filtering and drying the crystals to obtain the complex of Garcinol and Cyclodextrin.

In still another embodiment of the present invention the solvent is selected from a group comprising water, aliphatic alcohols with carbon atoms ranging from 1 to 4 and any combination thereof.

In still another embodiment of the present invention, the Cyclodextrin is selected from a group comprising α-cyclodextrin, β-cyclodextrin, 2-Hydroxy-propyl-β-cyclodextrin and derivatives thereof.

In still another embodiment of the present invention the cooling of the clear solution is to a temperature ranging from about 0° C. to about 25° C.

In still another embodiment of the present invention, the drying is carried out under vacuum.

In still another embodiment of the present invention the drying is carried out at a temperature ranging from about 75° C. to about 80° C.

In still another embodiment of the present invention mole ratio of the Garcinol to the Cyclodextrin ranges from about 1:1 to about 1:4.5.

The present invention is also in relation to Garcinol of purity ranging from about 95% to about 99%.

The present invention is also in relation to a method for extracting Garcinol, said method comprising acts of,
 a) shredding dried rind of *Garcinia Indica* or *Garcinia Cambogia* or combination thereof;
 b) extracting the shredded rind using suitable solvent;
 c) filtering to remove the cellulosic material and obtain clear solution;
 d) passing the clear solution through absorbent column to segregate into different fractions and obtain yellow coloured fraction;
 e) concentrating the yellow coloured fraction to obtain a waxy material;
 f) treating the waxy material with a suitable solvent; and
 g) filtering and drying the treated waxy material to obtain the Garcinol.

In still another embodiment of the present invention the solvent in steps (b) and (f) is independently selected from a group comprising toluene, benzene, carbon tetrachloride, trichloromethane, trichloromethane, Petroleum ether, ether solvents and any combination thereof.

In still another embodiment of the present invention the absorbent column is neutral alumina.

The present invention is also in relation to a composition comprising complex of Garcinol and Cyclodextrin along with pharmaceutically acceptable excipients.

In still another embodiment of the present invention the pharmaceutically acceptable excipients are selected from a group comprising binders, disintegrants, diluents, lubricants, plasticizers, permeation enhancers, solubilizers and any combination thereof.

In still another embodiment of the present invention the composition is in a form selected from a group comprising tablet, capsule, powder, syrup, solution, aerosol and suspension.

The present invention is also in relation to a composition comprising pharmaceutically acceptable amount of complex of present invention or a composition of the present invention and any other compound which can improve condition of cardiac dysfunction or any composition comprising thereof.

The present invention is also in relation to a method of managing and treating conditions of cardiac dysfunction said method comprising act of administering pharmaceutically effective amount of complex of present invention or a composition of present invention to a subject in need thereof.

In still another embodiment of the present invention, the pharmaceutically effective amount ranges from about 1 mg/kg to about 100 mg/kg of body weight per day.

In still another embodiment of the present invention the cardiac dysfunction is induced by chemotherapy drugs selected from a group comprising Doxorubicin, anthracycline derivatives and protease inhibitors.

In still another embodiment of the present invention the cardiac dysfunction is induced by inotropic agents selected from a group comprising Isoproterenol and Digitalis.

In still another embodiment of the present invention the cardiac dysfunction is induced by conditions of increased peripheral resistance and pressure selected from a group comprising stenosis, hypertension, myocardial infarction, ischemic heart disease and cardiomyopathy.

In still another embodiment of the present invention the method prevents heart failure induced by cardiac dysfunction.

In still another embodiment of the present invention the subject is an animal, including human being.

The disclosure is further elaborated with the help of following examples. However, these examples should not be construed to limit the scope of the disclosure.

Example 1

1 kg of shade dried rind of *Garcinia* Indica is shredded into small pieces ranging from 2 mm to 20 mm in size and loaded on soxhlator and extracted with 10 liters of toluene at 100° C. reflux conditions for 8 hrs. The liquid extract is filtered through 100 mesh filter to remove all the cellulosic material and the clear liquid obtained is cooled to room temperature. The cooled liquid is passed through chromatographic column comprising of neutral alumina 60-120 mesh size and the fractions are collected. The fast moving yellow colored fraction is collected and concentrated under vacuum to a waxy solid and treated with ethyl alcohol under reflux, filtered and dried at 70° C. under vacuum conditions to constant weight. Yield of Garcinol was 28 grams. Assay purity by HPLC was 98.5% as shown in FIG. 1. HPLC method used is specified below:

Column: 250×4.6 mm C-18 Reverse Phase 5μ
Injection volume: 20 μl
UV Detection Wavelength: 313 nm
Mobile phase: 45 of 0.1% Phosphoric Acid & 55 of Acetonitrile Isocratic
Flow rate: 1 ml/min Example 2

10 kg of shade dried rind of *Garcinia Cambogia* is shredded into small pieces ranging from 2 mm to 20 mm in size and loaded on soxhlator and extracted with 100 liters of toluene at 100° C. reflux conditions for 8 hrs. The liquid extract is filtered through 100 mesh filter to remove all the cellulosic material and the clear liquid obtained is cooled to room temperature. The cooled liquid is passed through chromatographic column comprising of neutral alumina 60-120 mesh size and the fractions are collected. The fast moving yellow colored fraction is collected and concentrated under vacuum to a waxy solid and treated with 5 liters of isopropyl alcohol under reflux, filtered and dried at 70° C. under vacuum conditions to constant weight. Yield of Garcinol was 300 grams. Assay purity by HPLC method was 95%. HPLC method used was same as in Example 1.

Example 3

2500 ml of isopropyl alcohol is taken and 250 grams of β-cyclodextrin is added to this along with 60 grams of pure Garcinol. The mixture is refluxed at 79-82° C. and 1 liter of demineralized water was added under agitation. The complete dissolution of the mixture by formation of a clear solution is crucial for chemical complexation of Garcinol with β-cyclodextrin. Further reflux was carried out for 2 hrs. The solution was allowed to cool slowly for 3 hrs to 35° C. under agitation and further stirred for 2 hrs. The slurry was filtered out and dried under vaccum at 75° C. for 8 hrs to constant weight. Yield of cyclodextrin complexed Garcinol was 282 grams. Mole ratio of Garcinol to Cyclodextrin in the complex was 1:2.

Example 4

2000 ml of ethyl alcohol is taken and 250 grams of β-cyclodextrin is added to this along with 60 grams of pure Garcinol. The mixture is refluxed at 79-82° C. and 750 ml of demineralized water was added under agitation. The complete dissolution of the mixture by formation of a clear solution is crucial for chemical complexation of Garcinol with β-cyclodextrin. Further reflux was carried out for 2 hrs. The solution was allowed to cool slowly for 3 hrs to 35° C. under agitation and further stirred for 2 hrs. The slurry was filtered out and dried under vacuum at 75° C. for 8 hrs to constant weight. Yield of cyclodextrin complexed Garcinol was 270 grams. Mole ratio of the chemical complexation of Garcinol to cyclodextrin was 1:2.

Example 5

200 grams of α-cyclodextrin is added to 1 liter of 70:30 isopropyl alcohol and water mixture under reflux conditions (80° C.). To this mixture, 25 grams of Garcinol is slowly added under agitation. The complete dissolution of the mixture by formation of a clear solution is crucial for chemical complexation of Garcinol with α-cyclodextrin. Further addition of Garcinol induced precipitation. The resulting solution was slowly cooled to room temperature and stirred for 24 hrs. The solution was filtered and dried at 75 to 80° C. under vacuum to constant weight. Yield of cyclodextrin complexed Garcinol was 215 grams. Mole ratio of Garcinol to cyclodextrin in the complex was 1:4.5.

Example 6

132 grams of 2-Hydroxy-propyl-β-cyclodextrin was mixed with 375 ml of water and heated to 80° C. To this, 60 grams of Garcinol was slowly added over a period of 5 hrs until disappearance of Garcinol forming uniform yellow syrupy solution. The solution was maintained at 75 to 80° C. for further 1 hr and then started to cool to 50° C. to get a hazy solution. Addition of 500 ml of isopropyl alcohol induced precipitation and resulting solution was slowly cooled to 10° C. to completely precipitate the cyclodextrin complexed Garcinol. The product was filtered and dried at 75° C. under vacuum to constant weight. Yield of cyclodextrin complexed Garcinol was 190 grams. Mole ratio of Garcinol to cyclodextrin was 1:1.

Example 7: Water Solubility of Garcinol and Test Molecule

Garcinol is insoluble in water at room temperature. The water solubility of the test molecules prepared in Example 4, 5 and 6 were evaluated and the corresponding results at 35-40° C. are as follows:

2-Hydroxy-propyl-β-cyclodextrin complexed Garcinol: 75 mg/ml
β-cyclodextrin complexed Garcinol: 25 mg/ml
α-cyclodextrin complexed Garcinol: 5 mg/ml The test molecule consisting of chemically complexed Garcinol with cyclodextrin is highly water soluble. Hence the test molecule has increased water solubility and higher in-vivo bioavailability when compared to Garcinol.

Example 8: Comparison of Stability of Garcinol and Test Molecule

Samples of Garcinol extracted in Example 2 and 3-cyclodextrin complexed Garcinol prepared in Example 3 were kept for accelerated storage stability test as per ICH guidelines. The conditions are as follows:

Temperature of storage chamber: 40° C.
Relative Humidity: 75% Rh
Duration: 3 months Table 1 summarizes the results of the stability storage test. The assay purity of Garcinol was reduced by 22% with additional peaks emerging in the HPLC chromatogram. The purity of Garcinol in the β-cyclodextrin complex was only marginally reduced by about 0.06%, clearly showing the test molecule disclosed in the present disclosure increases the stability of Garcinol.

TABLE 1

ACCELERATED STORAGE STABILITY TEST OF GARCINOL AND TEST MOLECULE

| Samples | | Physical Properties | Assay Purity |
|---|---|---|---|
| Garcinol | Original Sample | Yellow solid | 95% |
| | After 3 Months | Yellow waxy solid | 73% (22% Reduction) |
| β-cyclodextrin complexed Garcinol | Original Sample | White free flowing powder | 21.5% |
| | After 3 Months | White free flowing powder | 20.9% (0.6% Reduction) |

Example 9: Activity of Garcinol Against Doxorubicin Induced Cardiac Dysfunction Doxorubicin induced cardiac dysfunction is associated with impaired $Ca^{2+}$ handling in the sarcoplasmic reticulum (SR) reducing the cardiac function (Arai et. al., 2000). The following experimentation shows that Garcinol protects cardiomyocytes from Doxorubicin induced cardiac dysfunction.

Male Wistar rats were pretreated with Garcinol at 10, 25, 50, 100 and 200 mg/kg (p.o.) for 18 days. On day 16, Doxorubicin at a dose of 10 mg/kg (i.v.) was administered intravenously. On day 18, animals were sacrificed. Doxorubicin administration induced a progressive and severe deterioration of the repolariztion phase as seen from the prolongation in QT and ST intervals indicating tachyarrythmias and increased risk of cardiomyopathy. Elevated oxidative stress on the heart was also seen from increased lipid peroxidation and decreased glutathione (GSH) concentrations.

TABLE 2

ANIMAL MORTATILY AT THERAPEUTIC DOSES OF GARCINOL

| Parameters | Normal Control | Doxorubicin Control | Garcinol (100 mg/kg) + Doxorubicin | Garcinol (200 mg/kg) + Doxorubicin |
|---|---|---|---|---|
| Number of Animals Deaths | 0/6 | 0/6 | 3/6 | 6/6 |

Results: No significant therapeutic effect was seen in animals treated with Garcinol at 10, 25 and 50 mg/kg (p.o.). Significant cardioprotective activity was seen only at doses starting from 100 mg/kg (p.o.) to 200 mg/kg (p.o.) of Garcinol. However at these doses animal mortality was observed indicating toxicity. Pretreatment with Garcinol (100 mg/kg p.o.) significantly normalized QT and ST intervals and prevented reduction in heart rate. Oxidative stress induced by Doxorubicin was also negated. In spite of the therapeutic benefits, the use of Garcinol for treatment of cardiac dysfunction is highly undesirable due to the associated toxicity.

TABLE 3

EFFECT OF GARCINOL ON DOXORUBICIN INDUCED CARDIAC DYSFUNCTION IN ANIMALS

| Parameters | Normal Control | Doxorubicin Control | Garcinol (100 mg/kg) + Doxorubicin |
|---|---|---|---|
| Difference in Heart Rate (bpm) | −22.25 ± 7.28 | −77.5 ± 19.63[###] | −48.0 ± 14.8 |
| Difference in QT interval (sec) | 0.0033 ± 0.0025 | 0.014 ± 0.0035[##] | 0.0015 ± 0.0017[**] |
| Difference in ST interval (sec) | 0.00012 ± 0.0014 | 0.0085 ± 0.0048[###] | 0.00037 ± 0.0009[***] | n = 6; Data represented at Mean ± SEM; Data analyzed using One Way ANOVA followed by Tukey's Multiple Comparison test for each parameter;

[###]$p < 0.01$ and

[##]$P < 0.01$ as compared to Normal Control group;

[***]$P < 0.001$ and

[**]$P < 0.01$ as compared to Doxorubicin Control group.

TABLE 4

ACTIVITY OF GARCINOL AGAINST DOXORUBICIN INDUCED OXIDATIVE STRESS IN ANIMALS

| Tissue Parameters | Normal Control | Doxorubicin Control | Garcinol (100 mg/kg) + Doxorubicin |
|---|---|---|---|
| Lipid Peroxidation (nmol of MDA/mg of Protein) | 2.93 ± 0.05 | 4.56 ± 0.47## | 1.69 ± 0.04** |
| Glutathione (μg/mg of protein) | 23.80 ± 0.89 | 16.10 ± 1.17## | 22.05 ± 1.031** | n = 4; Data represented at Mean ± SEM; Data analyzed using One Way ANOVA followed by Tukey's Multiple Comparison test for each parameter;
$P < 0.01$ as compared to Normal Control group;
**$P < 0.01$ as compared to Doxorubicin Control group.

Example 10: Cardioprotective Activity of Test Molecule in Doxorubicin Induced Cardiac Dysfunction Doxorubicin is a chemotherapy drug which induces impaired $Ca^{2+}$ handling in Sarcoplasmin Reticulum resulting in reduced cardiac function. The cardioprotective efficacy test molecule comprising chemically complexed Garcinol with cyclodextrin was evaluated.

Male Wistar rats were pretreated with 20 mg/kg (p.o.) of test molecule for 18 days. On day 16, Doxorubicin at a dose of 10 mg/kg (i.v.) was administered intravenously. On day 18, animals were sacrificed. Doxorubicin administration significantly reduced cardiac function as seen from decreased heart rate. It also induces significant prolongation of QT and ST intervals. Significant reduction of mean arterial blood pressure, systolic and diastolic blood pressures were observed. Elevated oxidative stress on the heart was also seen from increased lipid peroxidation and decreased glutathione (GSH) concentrations.

TABLE 5

EFFECT OF TEST MOLECULE ON DOXORUBICIN INDUCED CARDIAC DYSFUNCTION IN ANIMALS

| Parameter | Cyclodextrin Control | Cyclodextrin + Doxorubicin Control | Doxorubicin Control | Test Molecule (20 mg/kg) + Doxorubicin |
|---|---|---|---|---|
| Difference in Heart Rate (bpm) | 7.050 ± 4.370 | −34.87 ± 6.935# | −33.67 ± 15.96# | −14.83 ± 13.87 |
| Difference in QT interval (sec) | 0.0029 ± 0.00087 | 0.0225 ± 0.00091### | 0.0229 ± 0.00206### | 0.0124 ± 0.00200** |
| Difference in ST interval (sec) | 0.0018 ± 0.00033 | 0.014 ± 0.001025### | 0.015 ± 0.001497### | 0.0053 ± 0.00054** | n = 6; Data represented at Mean ± SEM; Data analyzed using One Way ANOVA followed by Tukey's Multiple Comparison test for each parameter;
$P < 0.001$ and
$P < 0.05$ as compared to Cyclodextrin Control group;
**$P < 0.01$ as compared to Doxorubicin Control group.

TABLE 6

EFFECT OF TEST MOLECULE ON HEMODYNAMIC INSULTS INDUCED BY CHONIC DOXORUBICIN ADMINISTRATION

| Parameter | Cyclodextrin Control | Cyclodextrin + Doxorubicin Control | Doxorubicin Control | Test Molecule (20 mg/kg) + Doxorubicin |
|---|---|---|---|---|
| Mean Arterial Blood Pressure (mm Hg) | 105.4 ± 1.785 | 89.26 ± 2.357### | 89.26 ± 1.837### | 97.34 ± 1.223* |
| Systolic Blood Pressure (mm Hg) | 112.3 ± 2.090 | 89.88 ± 4.507### | 89.44 ± 5.108### | 105.9 ± 2.606* |
| Diastolic Blood Pressure (mm Hg) | 94.00 ± 0.8114 | 76.83 ± 1.709### | 75.96 ± 3.611### | 88.74 ± 3.600* | n = 6; Data represented at Mean ± SEM; Data analyzed using One Way ANOVA followed by Bonferroni post hoc test for each parameter;
$P < 0.001$ as compared to Cyclodextrin Control group;
*$P < 0.05$ as compared to Doxorubicin Control group.

TABLE 7

ACTIVITY OF TEST MOLECULE AGAINST DOXORUBICIN
INDUCED OXIDATIVE STRESS IN ANIMALS

| Tissue Parameters | Cyclodextrin Control | Cyclodextrin + Doxorubicin Control | Doxorubicin Control | Test Molecule (20 mg/kg) + Doxorubicin |
|---|---|---|---|---|
| Lipid Peroxidation (nmol of MDA/mg of Protein) | 2.828 ± 0.1880 | 4.056 ± 0.2880[#] | 4.160 ± 0.3427[#] | 1.885 ± 0.09105** |
| Glutathione (μg/mg of protein) | 24.21 ± 1.072 | 16.76 ± 0.4971[###] | 17.29 ± 0.4496[###] | 21.46 ± 0.3441** | n = 4; Data represented at Mean ± SEM; Data analyzed using One Way ANOVA followed by Tukey's Multiple Comparison test for each parameter;
[###]$P < 0.01$ and
[##]$P < 0.01$ as compared to Cyclodextrin Control group;
**$P < 0.01$ as compared to Doxorubicin Control group.

Results: No animal mortality was observed in all the groups. Pretreatment with test molecule (20 mg/kg p.o.) significantly normalized QT and ST intervals and prevented reduction in heart rate. Significant reversal of Doxorubicin induced reduction in mean arterial blood pressure, systolic and diastolic blood pressures were observed. Oxidative stress induced by Doxorubicin was negated by the test molecule.

The therapeutic potential of the test molecule at a dose of 20 mg/kg is comparable to that of administration of 100 mg/kg (p.o.) of Garcinol as seen in Example 9. This confirms that the chemical complexing of Garcinol with Cyclodextrin increases its therapeutic index by making it more efficacious. Moreover, this activity of the test molecule was achieved without any mortality of the animals indicating elimination of toxicity. Hence, the above examples demonstrate a significant enhancement of therapeutic characteristics of the test molecule in treating cardiac dysfunction induced by Doxorubicin.

Example 11: Effect of Test Molecule in Chronic Administration of Doxorubicin

The efficacy of the test molecule in managing the cardiac dysfunction side effects induced by chronic administration of Doxorubicin was evaluated. This study was designed in view of potential use of Doxorubicin for chronic administration in cancer treatment without its cardiotoxic side effects.

Male Wistar rats were pretreated with 20 mg/kg (p.o.) of test molecule for 30 days. On days 1, 7, 14, 21 and 28, Doxorubicin at a dose of 3 mg/kg (i.p.) was administered intravenously. On Day 30, animals were sacrificed for histopathological examination of the heart.

Results: Pretreatment with test molecule significantly normalized prolongation of QT, ST and QTc intervals induced by Doxorubicin and prevented reduction in heart rate. Improvement was observed in mean arterial blood pressure, systolic and diastolic blood pressures. Reduction in oxidative stress was evident from increased GSH level and decreased lipid peroxidation in comparison with Doxorubicin control group. Protection against Doxorubicin induced myocardial injury was seen in histopathological examination of the heart. The test molecule significantly reduced Myocardial Necrosis, Inflammation, Cytoplasmic Vacuoles, Cytoplasmic Eosinophilia, and Vascular Congestion.

TABLE 8

EFFECT OF TEST MOLECULE ON CARDIAC DYSFUNCTION
INDUCED BY CHRONIC DOXORUBICIN ADMINISTRATION

| Parameter | Cyclodextrin Control | Cyclodextrin + Doxorubicin Control | Doxorubicin Control | Test Molecule (20 mg/kg) + Doxorubicin |
|---|---|---|---|---|
| Difference in Heart Rate (bpm) | 16.38 ± 13.77 | −66.22 ± 8.303[##] | −64.59 ± 12.13[##] | −16.97 ± 25.69 |
| Difference in QT interval (sec) | 0.0025 ± 0.0010 | 0.015 ± 0.00437[##] | 0.015 ± 0.00087[##] | 0.0034 ± 0.0017* |
| Difference in ST interval (sec) | 0.0015 ± 0.001 | 0.016 ± 0.0022[###] | 0.016 ± 0.0015[###] | 0.005 ± 0.00047*** |
| Difference in QTc interval (sec) | 0.007 ± 0.0018 | 0.033 ± 0.0092[##] | 0.035 ± 0.0046[##] | 0.012 ± 0.0017* | n = 6; Data represented at Mean ± SEM; Data analyzed using One Way ANOVA followed by Tukey's Multiple Comparison test for each parameter;
[###]$P < 0.001$ and
[##]$P < 0.01$ as compared to Cyclodextrin Control group;
***$P < 0.001$ and
*$P < 0.05$ as compared to Doxorubicin Control group.

TABLE 9

EFFECT OF TEST MOLECULE ON HEMODYNAMIC INSULTS
INDUCED BY CHONIC DOXORUBICIN ADMINISTRATION

| Parameter | Cyclodextrin Control | Cyclodextrin + Doxorubicin Control | Doxorubicin Control | Test Molecule (20 mg/kg) + Doxorubicin |
|---|---|---|---|---|
| Mean Arterial Blood Pressure (mm Hg) | 108.2 ± 2.522 | 88.04 ± 1.813### | 86.67 ± 0.9226### | 101.0 ± 3.525** |
| Systolic Blood Pressure (mm Hg) | 117.8 ± 2.871 | 92.22 ± 2.275### | 92.59 ± 1.728### | 103.6 ± 0.8007** |
| Diastolic Blood Pressure (mm Hg) | 97.13 ± 2.149 | 80.00 ± 2.298### | 82.81 ± 1.997### | 93.47 ± 1.783** | n = 6; Data represented at Mean ± SEM; Data analyzed using One Way ANOVA followed by Tukey's Multiple Comparison test for each parameter;
$p < 0.01$ as compared to Cyclodextrin Control group;
**$P < 0.01$ as compared to Doxorubicin Control group.

TABLE 10

ACTIVITY OF TEST MOLECULE AGAINST OXIDATIVE STRESS
INDUCED BY CHRONIC DOXORUBICIN ADMINISTRATION

| Tissue Parameters | Cyclodextrin Control | Cyclodextrin + Doxorubicin Control | Doxorubicin Control | Test Molecule (20 mg/kg) + Doxorubicin |
|---|---|---|---|---|
| Lipid Peroxidation (nmol of MDA/mg of Protein) | 2.265 ± 0.3640 | 4.700 ± 0.6126### | 4.631 ± 0.3671### | 1.819 ± 0.1594** |
| Glutathione (μg/mg of protein) | 23.32 ± 1.822 | 15.15 ± 0.6584### | 15.05 ± 0.8970### | 22.02 ± 0.5888** | n = 4; Data represented at Mean ± SEM; Data analyzed using One Way ANOVA followed by Tukey's Multiple Comparison test for each parameter;
$P < 0.01$ as compared to Cyclodextrin Control group;
**$P < 0.01$ as compared to Doxorubicin Control group.

TABLE 11

HISTOPATHOLOGICAL EXAMINATION OF HEART OF TEST ANIMALS
AFTER CHRONIC DOXORUBICIN ADMINISTRATION

| Treatment Group | Myocardial necrosis | Inflammation | Cytoplasmic vacuoles | Cytoplasmic Eosinophilia | Vascular congestion |
|---|---|---|---|---|---|
| Cyclodextrin Control | -- | -- | -- | --- | --- |
| Cyclodextrin + Doxorubicin Control | +++ | +++ | ++ | ++ | ++ |
| Doxorubicin Control | +++ | +++ | ++ | +++ | ++ |
| Test Molecule (20 mg/kg) + Doxorubicin | + | + | + | + | + | n = 4; Grading System used for assessment of above parameters: (—) No Changes, (+) 5-30% of cells show changes, (++) 30-60% of cells show changes and (+++) 60-90% of cells show changes.

Based on the results of the above experiments, it has been clearly shown that the test molecule can be effectively used in combination with Doxorubicin for effectively minimizing the cardiotoxic side effects and enabling increased dosage and treatment regimen of the chemotherapy.

Example 12: Cardioprotective Activity of Test Molecule in Digitalis Induced Cardiac Dysfunction Digitalis is used in treatment of atrial fibrillation, flutter and congestive heart failure. It has dose dependent toxicity limitation. At high doses, Digitalis induces irregular heartbeat, ectopic atrial tachycardia and cardiac arrest. This study was conducted to evaluate the potential protective activity of test molecule against Digitalis induced cardiac dysfunction, thereby enabling increase in dosage of Digitalis.

Male Wistar rats were pretreated with 20 mg/kg (p.o.) of test molecule for 18 days. On Day 18, Digitalis at a three doses of 500 mg/kg/interval was administered intravenously with interval period of 15 min. After this, 200 mg/kg/interval was administered every 15 min continued upto cardiac arrest. Histopathological examination of the heart was conducted.

Results: Pretreatment with test molecule significantly increased the dose of Digitalis required to produce ectopic beat, atrial fibrillation, and cardiac arrest. Test molecule also reduced Digitalis induced oxidative stress as seen from increased GSH level and decreased Lipid Peroxidation when compared to Digitalis control group. Histopathological examination revealed that test molecule significantly reduced Myocardial Necrosis, Inflammation, Cytoplasmic Vacuoles, Cytoplasmic Eosinophilia, and Vascular Congestion, thereby protecting myocardial tissue against Digitalis induced cardiac dysfunction.

TABLE 12

EFFECT OF TEST MOLECULE ON DIGITALIS DOSE (μg/kg) REQUIRED TO INDUCE CARDIAC DYSFUNCTION IN ANIMALS

| Dose of Digitalis (μg/kg) required for inducing the following | Digitalis Control | Test Molecule + Digitalis |
|---|---|---|
| Ectopic Beats | 2700 ± 212.9 | 3517 ± 183.3* |
| Arterial Fibrillation | 2933 ± 233.3 | 3833 ± 204.4* |
| Cardiac Arrest | 3067 ± 280.1 | 4000 ± 240.8* | n = 6; Data represented as Mean ± S.E.M. Data analyzed using Mann Whitney Test for each parameter.
*P < 0.05 as compared to Digitalis Control group.

TABLE 13

ACTIVITY OF TEST MOLECULE AGAINST DIGITALIS INDUCED OXIDATIVE STRESS IN ANIMALS

|  | Digitalis Control (Mean ± S.E.M) | Test Molecule + Digitalis (Mean ± S.E.M) |
|---|---|---|
| Lipid Peroxidation (nmol of MDA/mg of Protein) | 6.909 ± 0.4459 | 3.860 ± 0.2146*** |
| Glutathione (μg/mg of protein) | 21.01 ± 0.5369 | 28.68 ± 0.8343*** | n = 4; Data represented as Mean ± S.E.M. Data analyzed using Unpaired t-test for each parameter.
***P < 0.001 as compared to Digitalis Control group.

TABLE 14

HISTOPATHOLOGICAL EXAMINATION OF HEART OF TEST ANIMALS WITH DIGITALIS INDUCED CARDIAC DYSFUNCTION

| Treatment Group | Myocardial necrosis | Inflammation | Cytoplasmic vacuoles | Cytoplasmic Eosinophilia | Vascular congestion |
|---|---|---|---|---|---|
| Digitalis Control | +++ | +++ | ++ | ++ | ++ |
| Test Molecule + Digitalis | + | + | + | + | + | n = 4; Grading System used for assessment of above parameters: (−−) No Changes; (+) 5-30% of cells show changes; (++) 30-60% of cells show changes and (+++) 60-90% of cells show changes.

Based on the results of the above experiment, it is concluded that the test molecule protects from Digitalis induced cardiac dysfunction. When used in combination, the test molecule will enable increase in the dose of Digitalis used in treatment thereby enhancing its therapeutic effects.

Example 13: Cardioprotective Activity of Test Molecule in Isoproterenol Induced Cardiac Dysfunction The protective activity of test molecule against Isoproterenol induced cardiac dysfunction was evaluated as follows.

Male Wistar rats were pretreated with 20 mg/kg (p.o.) of test molecule 18 days. From Day 9, Isoproterenol at a dose of 1 mg/kg/day was administered intravenously for 10 days. Isoproterenol administration induced significant changes to the QT and ST interval. Isoproterenol induced oxidative stress was observed by decreased Glutathione (GSH) and increased lipid peroxidation concentrations in the heart.

Results: Pretreatment with test molecule significantly normalized QT, ST intervals and prevented reduction in heart rate. Improvement was also observed in mean arterial blood pressure. Reduction in oxidative stress was also observed.

TABLE 15

CARDIOPROTECTIVE ACTIVITY OF TEST MOLECULE AGAINST ISOPROTERENOL
INDUCED CARDIAC DYSFUNCTION IN ANIMALS

| Parameters | Normal Control | Cyclodextrin Control | Isoproterenol Control | Test Molecule + Isoproterenol |
|---|---|---|---|---|
| Difference in Heart Rate (bpm) | 16.68 ± 1.667 | 9.117 ± 7.189 | 43.66 ± 6.267 | 24.72 ± 4.81 |
| Difference in QT Interval (sec) | 0.0022 ± 0.0004 | 0.00088 ± 0.00085 | 0.01686 ± 0.002### | 0.0054 ± 0.001*** |
| Difference in ST Interval (sec) | 0.00172 ± 0.00085 | 0.00415 ± 0.00081 | 0.0180 ± 0.0009### | 0.006 ± 0.0008*** |
| Mean Arterial Blood Pressure (mm Hg) | 86.35 ± 3.031 | 87.93 ± 4.478 | 72.45 ± 5.942 | 85.48 ± 3.076 | n = 5; Data represented as Mean ± S.E.M. Data analyzed using One Way ANOVA followed by Bonferroni post hoc test for each parameter.
$P < 0.001$ as compared to Cyclodextrin Control group;
***$P < 0.001$ as compared to Isoproterenol Control group.

TABLE 16

ACTIVITY OF TEST MOLECULE AGAINST OXIDATIVE STRESS
INDUCED BY ISOPROTERENOL ADMINISTRATION

| Tissue Parameters | Normal Control | Cyclodextrin Control | Isoproterenol Control | Test Molecule (20 mg/kg) + Isoproterenol |
|---|---|---|---|---|
| Lipid Peroxidation (nmol of MDA/mg of Protein) | 2.690 ± 0.2154 | 4.130 ± 0.1468 | 4.443 ± 0.0392 ### | 3.47 ± 0.1646** |
| Glutathione (μg/mg of protein) | 27.50 ± 1.501 | 20.37 ± 0.8556 | 19.02 ± 0.8526 ## | 23.49 ± 1.471 | n = 4; Data represented as Mean ± S.E.M. Data analyzed using One Way ANOVA followed by Bonferroni post hoc test for each parameter.
$P < 0.001$ and
$P < 0.01$ as compared to Cyclodextrin Control group;
**$P < 0.01$ as compared to Isoproterenol Control group.

Based on the results of the above experiment, it is concluded the test molecule protects the heart from Isoproterenol induced cardiac dysfunction. Hence, when used in combination with Isoproterenol the test molecule increases the therapeutic potential of Isoproterenol.

Example 14: Activity of Test Molecule in Aortic Stenosis Induced Congestive Cardiac Dysfunction in Animals Aortic banding (stenosis) creates a pressure overload on the heart by narrowing the aorta. Takizawa et. al. (1999), has reported that under conditions of pressure-overload there is a reduction in transcription of SERCA2 mRNA expression which decreases SERCA2 protein concentration and in turn decreases $Ca^{2+}$ uptake in the SR. This result in reduced cardiac function characterised by an initial increase in blood pressure indicating compensating mechanism of the heart to pump more blood, followed by a fall in the blood pressure and finally causing congestive heart failure. The effect of the test molecule is protecting the heart from congestive heart failure was evaluated in this experiment.

Male Wistar rats weighing 220 to 300 gm were anesthetized with Thiopental 25 mg/kg (i.p.) and aortic constriction was created via a Left Thoracotomy by placing a ligature using sterilized silk suture of size 4-0 securely around the ascending aorta and a 40 mm long cannula of diameter 0.9 mm was placed longitudinally to the aorta & tied with it. Then cannula was slowly removed, leaving an aortic lumen of 0.9 mm diameter. Treatment with test molecule was carried out for 18 days before the surgery and was continued for 4 weeks after the surgery.

Results: Pretreatment with test molecule significantly prevented reduction in heart rate induced by aortic stenosis and normalized QT, ST and QTc intervals. Improvements were observed in mean arterial blood pressure, systolic and diastolic blood pressures. The test molecule significantly reduced aortic stenosis induced cardiac dysfunction as measured by heart weight to body weight ratio and left ventricular weight to body weight ratio. Reduction in oxidative stress was also observed.

TABLE 17

CARDIOPROTECTIVE ACTIVITY OF TEST MOLECULE AGAINST AORTIC STENOSIS INDUCED COGESTIVE CARDIAC DYSFUNCTION IN ANIMALS

| Parameters | Normal Control | Sham Control | Stenosis Control | Test Molecule + Stenosis |
|---|---|---|---|---|
| Difference in Heart Rate (bpm) | 4.583 ± 7.413 | −13.05 ± 12.83 | −88.79 ± 12.31### | −45.64 ± 4.673* |
| Difference in QT Interval (sec) | −0.001183 ± 0.0006 | −0.0011 ± 0.0009$^{ns}$ | 0.018 ± 0.0013### | 0.0067 ± 0.0016*** |
| Difference in ST Interval (sec) | −0.00125 ± 0.00168 | −0.0025 ± 0.0018$^{ns}$ | 0.0144 ± 0.001### | 0.0063 ± 0.0021* |
| Difference in QTc Interval (sec) | 0.003167 ± 0.002227 | 0.004667 ± 0.004279$^{ns}$ | 0.0260 ± 0.007232### | 0.004167 ± 0.003429* | n = 6; Data represented as Mean ± S.E.M. Data analyzed using One Way ANOVA followed by Bonferroni post hoc test for each parameter.

$^{ns}$not significant as compared to Normal Control group;

$P < 0.001$ as compared to Sham Control group;

***$P < 0.001$ and

*$P < 0.05$ as compared to Stenosis Control group.

TABLE 18

EFFECT OF TEST MOLECULE ON HEMODYNAMIC INSULTS INDUCED BY AORTIC STENOSIS

| Parameter | Normal Control | Sham Control | Stenosis Control | Test Molecule + Stenosis |
|---|---|---|---|---|
| Mean Arterial Blood Pressure (mm Hg) | 78.35 ± 3.408 | 71.70 ± 4.419$^{ns}$ | 98.46 ± 2.999### | 88.40 ± 2.491 |
| Systolic Blood Pressure (mm Hg) | 87.07 ± 3.808 | 79.09 ± 4.832$^{ns}$ | 112.6 ± 3.312### | 97.49 ± 2.173 |
| Diastolic Blood Pressure (mm Hg) | 77.42 ± 3.963 | 69.77 ± 4.872$^{ns}$ | 96.93 ± 2.327### | 88.32 ± 2.685 | n = 6; Data represented as Mean ± S.E.M. Data analyzed using One Way ANOVA followed by Bonferroni post hoc test for each parameter.

$^{ns}$not significant as compared to Normal Control group;

$P < 0.001$ as compared to Sham Control group.

TABLE 19

ACTIVITY OF TEST MOLECULE AGAINST AORTIC STENOSIS INDUCED CARDIAC DYSFUNCTION IN ANIMALS

| Parameters | Normal Control | Sham Control | Stenosis Control | Test Molecule + Stenosis |
|---|---|---|---|---|
| Heart Weight/Body Weight (mg/g) | 3.135 ± 0.078 | 2.985 ± 0.0769 (ns) | 4.085 ± 0.037 ### | 3.42 ± 0.0486*** |
| Left Ventricular Weight/Body Weight (mg/g) | 1.516 ± 0.023 | 1.569 ± 0.0305 (ns) | 1.968 ± 0.0324 ### | 1.711 ± 0.0312*** | n = 6; Data represented as Mean ± S.E.M. Data analyzed using One Way ANOVA followed by Bonferroni post hoc test for each parameter.

(ns)—not significant as compared to Normal Control group;

$P < 0.001$ as compared to Sham Control group;

*** $P < 0.001$ as compared to Stenosis Control group.

TABLE 20

ACTIVITY OF TEST MOLECULE AGAINST OXIDATIVE
STRESS INDUCED BY AORTIC STENOSIS

| Tissue Parameter | Normal Control | Sham Control | Stenosis Control | Test Molecule + Stenosis |
|---|---|---|---|---|
| Lipid Peroxidation (nmol of MDA/mg of Protein) | 2.729 ± 0.1250 | 3.399 ± 0.2121$^{ns}$ | 4.546 ± 0.1797$^{\#\#\#}$ | 3.458 ± 0.9755** |
| Glutathione (µg/mg of protein) | 30.39 ± 1.605 | 26.09 ± 0.6497$^{ns}$ | 18.73 ± 0.7187$^{\#\#\#}$ | 25.53 ± 1.700* | n = 4; Data represented as Mean ± S.E.M. Data analyzed using One Way ANOVA followed by Bonferroni post hoc test for each parameter.
$^{ns}$not significant as compared to Normal Control group;
$^{\#\#\#}$P < 0.001 as compared to Sham Control group;
***P < 0.001 and
*P < 0.05 as compared to Stenosis Control group.

Aortic stenosis model represents a condition of cardiac dysfunction caused by increased peripheral resistance leading to pressure overload. This condition can be induced by other physiological disease conditions like hypertension, atherosclerosis, myocardial infarction, ischemic heart disease and cardiomyopathy. Hence the above experiment shows that the test molecule will be effective in the treatment and management of cardiac dysfunction induced by pressure overload.

We claim:

1. A method of managing and treating conditions of drug induced cardiac dysfunction, said method comprising the steps of administering a physiologically effective amount of complex comprising garcinol and cyclodextrin, wherein the mole ratio of the garcinol to the cyclodextrin is about 1:4.5 or a composition comprising garcinol and cyclodextrin, optionally along with a pharmaceutically acceptable excipient, wherein the mole ratio of the garcinol to the cyclodextrin is about 1:4.5, to a subject in need thereof, wherein the drug induced dysfunction is induced by a drug selected from the group consisting of: doxorubicin, anthracycline derivatives, isoproterenol and *digitalis*.

2. The method as claimed in claim 1, wherein the physiologically effective amount ranges from about 1 mg/kg to about 100 mg/kg of body weight per day.

3. The method as claimed in claim 1, wherein the cardiac dysfunction is selected from the group consisting of drug induced tachycardia, drug induced cardiomyopathy, drug induced cardiac arrest, drug induced ischemic heart disease, drug induced heart failure, myocardial infarction, drug induced tachyarrhythmia, drug induced elevated oxidative stress, and drug induced cardio toxicity.

4. The method as claimed in claim 1, wherein the drug induced cardiac dysfunction is selected from the group consisting of abnormal progression in ST and QT interval, irregular heart rate, impairment in mean arterial blood pressure, impairment in systolic arterial blood pressure, impairment in diastolic arterial blood pressure, hypertension, stenosis, and myocardial injury.

5. The method as claimed in claim 1, wherein the method protects against heart failure caused by drug induced cardiac dysfunction, reduces drug induced oxidative stress, and manages drug induced cardio toxicity.

6. The method as claimed in claim 1, wherein the cyclodextrin is selected from the group consisting of α-cyclodextrin, β-cyclodextrin, and 2-hydroxy-propyl-β-cyclodextrin.

7. The method as claimed in claim 1, wherein the pharmaceutically acceptable excipient is selected from the group consisting of binders, disintegrants, diluents, lubricants, plasticizers, permeation enhancers, and solubilizers, and any combination thereof.

8. The method as claimed in claim 1, wherein the composition is in a form selected from the group consisting of tablet, capsule, powder, syrup, solution, aerosol, and suspension.

9. The method as claimed in claim 1, wherein the subject is an animal, including a human being.

10. The method as claimed in claim 1, wherein the physiologically effective amount is preferably about 20 mg/kg of body weight per day.

11. The method as claimed in claim 1, wherein the cyclodextrin is β-cyclodextrin.

* * * * *